United States Patent [19]

Hourihan et al.

[11] Patent Number: 4,704,271

[45] Date of Patent: Nov. 3, 1987

[54] WATER-IN-OIL EMULSION ANTIPERSPIRANT STICK

[75] Inventors: Joseph C. Hourihan, Little Falls, N.J.; Helga Krevald, Tarrytown, N.Y.

[73] Assignee: American Cyanamid Company, Stamford, Conn.

[21] Appl. No.: 815,283

[22] Filed: Dec. 26, 1985

Related U.S. Application Data

[63] Continuation of Ser. No. 596,077, Apr. 3, 1984, abandoned, which is a continuation of Ser. No. 353,732, Mar. 1, 1982, abandoned.

[51] Int. Cl.$^4$ .......................... A61K 7/32; A61K 7/34; A61K 7/36; A61K 7/38

[52] U.S. Cl. ................................ 424/66; 424/DIG. 5; 424/67; 424/68

[58] Field of Search ...................... 424/DIG. 5, 65, 66, 424/67, 68

[56] References Cited

U.S. PATENT DOCUMENTS

| | | | |
|---|---|---|---|
| 3,541,205 | 11/1970 | Hardigan et al. | 424/68 |
| 4,264,586 | 4/1981 | Callingham et al. | 424/68 |
| 4,265,878 | 5/1981 | Keil | 424/DIG. 5 |
| 4,268,499 | 5/1981 | Keil | 424/DIG. 5 |
| 4,350,605 | 9/1982 | Hughetl | 424/68 |

FOREIGN PATENT DOCUMENTS 2852988  6/1979  Fed. Rep. of Germany ... 424/DIG. 5

OTHER PUBLICATIONS

Ash et al, 1977, Formulary of Cosmetic Preparations, pp. 5 to 7, 16 and 23 to 25.

*Primary Examiner*—Dale R. Ore
*Attorney, Agent, or Firm*—C. J. Fickey

[57] ABSTRACT

Antiperspirant compositions containing an aqueous solution of an astringent compound as a discontinuous or dispersed phase in a solid matrix of a volatile silicone, a solid alkanol containing at least 12 carbon atoms, a $C_4$ to $C_8$ alkylene diol, and a saturated $C_{12}$ to $C_{20}$ fatty acid ester of at least one polyglycerol emulsifying agent having a resultant HLB value of 6 to 9. The compositions may also contain an alkanoic acid having at least 12 carbon atoms.

7 Claims, No Drawings

WATER-IN-OIL EMULSION ANTIPERSPIRANT STICK

This application is a continuation of application Ser. No. 596,077, filed Apr. 3, 1984, which is a continuation of Ser. No. 353,732, filed Mar. 6, 1982, both aband.

The present invention relates to improvements in bases useful for cosmetic and pharmaceutical preparations in general, and to antiperspirant compositions in particular. Still more particularly, it relates to antiperspirant stick compositions of the so-called "dry-feeling" type comprising water-in-oil emulsions of an astringent compound in a solid matrix generally comprising a low-melting wax and an oil, and more particularly, a volatile silicone and/or other oils and stearyl alcohol, as the hydrophobic continuous phase.

Liquid antiperspirant products are well-known both in the prior art and in the market place. Historically, they have been of two principal types—the solution type and the alcohol-in-water type, both of which have disadvantages. The former are tacky and the latter are perceived as cold on application and cause a stinging sensation due to the alcohol.

Many attempts have been made to provide efficacious antiperspirants of the "dry-feeling" type and these usually comprise water-insoluble, non-polar, volatile silicone compounds, as disclosed, for example, by Davy et al, U.S. Pat. No. 4,126,679, and Geary et al, U.S. Pat. No. 4,151,272.

It has long been known that aqueous solutions of antiperspirant astringents, such as aluminum chlorohydrate, are more efficacious than dry powders or aerosols.

However such compositions, where water is the continuous phase, for example, an aqueous solution of astringent or an oil-in-water emulsion thereof, are less desirable for the reasons given above, that is, they feel wet when applied to the skin and tend to go through a tacky stage during drying after application.

Gee et al, U.S. Pat. No. 4,122,029, and Keil, U.S. Pat. No. 4,265,878, describe water-in-oil emulsion type antiperspirant compositions in which an aqueous solution of an astringent is emulsified in a non-polar continuous phase, for example, a volatile silicone. These compositions are reported to have the desired "dry" feel, improved efficacy, and do not exhibit the wet and tacky effect which is characteristic of aqueous solutions of the astringent.

The water-in-oil type antiperspirant compositions of Gee et al and Keil essentially comprise an aqueous solution of an astringent compound emulsified in a volatile silicone continuous phase. Gee et al use a silicon-free water-in-oil surfactant having an HLB (Hydrophilic-Lipophilic Balance) value of 2 to 10, and certain polydiorganosiloxane-polyoxyalkylene block copolymers as the emulsifying agents. Keil found that, although the compositions of Gee et al may be formulated as lotions, gels and sprays, the preparation of stick-forming compositions therefrom, which do not separate in the molten state and which solidify to a non-leaking stick, are not successful with conventional techniques of using singular gelling agents. Keil found that good antiperspirant sticks are obtained by mixing a stick-forming mixture of components consisting essentially of a solid alkanoic acid, for example, stearic acid, and a waxy ester, for example, spermaceti wax, and, optionally, up to three parts by weight of a solid alkanol, for example, stearyl alcohol, for every one part by weight of waxy ester. The solid alkanoic acid reportedly serves as an auxillary water-in-oil type surfactant, while the waxy ester reportedly has better compatibility with the primary surfactant, that is, the polydiorganosiloxane-polyoxyalkylene block copolymer of Gee et al, and the volatile silicone liquid, than do the solid alkanols usually used in stick formulations.

It is an object of the present invention to provide dry-feeling, stable, water-in-oil emulsion type anti-perspirant stick compositions using conventional gelling agents.

It is another object of the invention to provide water-in-oil emulsion type antiperspirant stick compositions which are stable in the molten and solid state, wherein the emulsion is at or near the breaking point and which breaks upon application, or slightly thereafter, to provide good application properties and which delivers the antiperspirant active efficiently, providing good efficacy.

It is another object of the invention to provide water-in-oil emulsion type antiperspirant stick compositions which exhibit increased antiperspirant efficacy.

These objectives are met in accordance with the present invention by forming an emulsion of an aqueous solution of an astringent compound in a non-polar matrix as the continuous phase, in which the continuous phase consists essentially of said volatile silicone, a solid alkanol gelling agent, a C4 to C8 alkanediol and at least one water-in-oil emulsifier of the polyglyceryl ester type having an HLB value of 6 to 9.

The compositions of the invention differ from the prior art compositions of the water-in-oil emulsion type in that a gelling agent of the conventional solid alkanol type is used, which is compatible with the polyglyceryl ester emulsifier, to provide stable, dry-feeling solid sticks. The compositions also differ from the prior art compositions in that enhanced antiperspirant efficacy is obtained by the incorporation of a C4 to C8 alkanediol compound.

The compositions of the invention consist essentially of (a) 10 to 70 parts by weight of an aqueous solution of an astringent as the discontinuous, or dispersed, phse in a solid matrix consisting essentially of (b) about 0.1 to 35 parts by weight of a volatile silicone liquid, (c) about 10 to 30 parts by weight of t lest one solid alkanol containing at least 12 carbon atoms, (d) about 1 to 5 parts by weight of a C4 to C8 alkylene diol, and (e) about 0.5 to 5 parts by weight of at least one saturated C12 to C20 fatty acid ester of a polyglycerol emulsifying agent having a resultant HLB value of 6 to 9. The compositions may optionally contain up to about 5 parts by weight of an alkanoic acid having at least 12 carbon atoms.

Component (a) is an aqueous solution of any astringent antiperspirant agent. Examples of well-known astringents include aluminum sulfate, aluminum chloride, aluminum chlorohydrate, aluminum sulfocrbolate, aluminum-zirconium chlorohydrate, zinc chloride, zinc sulfocarbolate, zinc sulfate, zirconium salts, such as zirconium chlorohydrate, combinations of aluminum chloride and aluminum-zirconium chlorohydrate, aluminum-zirconium chlorohydroglycine, and the like.

The amount of astringent that is dissolved in water to form component (a) may vary widely and is not critical; however, certain practical limitations exist. On the one hand, an efficacious antiperspirant composition should contain sufficient stringent to provide sweat reduction;

on the other hand, it is desirable to maximize the amount of water in the formulation without negating utility. Preferably, the antiperspirant compositions will comprise bout 15 to 30-weight percent astringent, on a solids bsis although compositios containing less than 15-weight percent are useful as personal care products. Depending on the particular astringent used, component (a) may vary in concentration from as little as 15 parts by weight of stringent per 100 parts by weight of water up to a saturated solution thereof. For practical purposes, a particularly useful component (a) consists of an aqueous solution of equal weight portions of aluminum chlorohydrate and water.

The volatile liquid component (b) is a fluid, non-polar methylsiloxane. The volatile liquid should have a boiling point at atmospheric pressure of less than about 250° C. and preferably between about 100° C. and 200° C. The volatile methylsiloxanes are oligomers, that is, they comprise dimethylsiloxne units $[(CH3)2SiO]_x$, of which the cyclic tetramer, pentamer and hexamer (X=4,5,6) are preferred. Specific compounds include 2,4,6,8-octamethylcyclotetrasilane, 2,4,6,8,10-decamethylcyclopentasiloxane, and 2,4,6,8,10,12-dodecamethylcyclohexasiloxane, and mixtures thereof.

The cyclic silicones are isolated from the hydrolysis product of dimethyldichlorosilane; see Patnode, Wilcock, *J. Am. Chem. Soc.* 68, 358 (1946).

Component (c) is a solid waxy material commonly used in the cosmetic art and this component comprises the primary gelling agent for the stick compositions. The solid waxy material should have a melting point above 20° C. and preferably below 90° C. Examples include stearyl and cetyl alcohols, syncrowax, polyethylene wax, and mixtures thereof. Stearyl alcohol is preferred.

Component (d), which is incorporated into the stick composition to boost or enhance the antiperspirant efficacy, is a C4 to C8 alkanediol. The preferred compound is 2-methyl-2,4-pentanediol. Other useful alkanediols include 1,2- and 1,3-propanediol, 1,2- and 1,3-butanediol, 2,4-pentanediol, 2,3-hexanediol, 1,3-hexanediol, 2,3-butanediol, 4,5-octanediol, and the like.

The emulsifying agent, component (c), is a C12 to C20 saturated ester of a polyglycerol containing from about 2 to 10 glycerol units. In order for the preparation of stable water-in-oil emulsions with optimum application aesthetics, the emulsifying system should have a resultant HLB value of 6-9, inclusive (see Griffen, *J. Soc. Cosmetic Chemists* 1,311 (1949) and *The Atlas HLB System*, Communique, Atlas Chemical Ind., Inc., 4th Printing.) Such emulsifying agents include polyglyceryl-3-isostearate, polyglyceryl-4-isostearate, polyglyceryl-3-stearate, polyglyceryl-5-stearate, polyglyceryl-4-palmitate, polyglyceryl-6-palmitate, polyglyceryl-3-laurate, polyglyceryl-3-myristate, and the like.

An alkanoic acid having at least 12 carbon atoms, such as stearic acid, may also be incorporated into the stick composition as an emulsion stabilizer and to aid in efficacy. Stable emulsions are obtained if this component is omitted; however, its inclusion is preferred.

The compositions of the invention may also comprise minor amounts of nonessential components which are commonly used in the cosmetic art, such as colorants, fragrances, humectants, hydrocarbon waxes, clays, such as the Bentones, additional emollients, and the like.

The best preparative method currently known is to form a warm solution (60°-75° C.) of components (b) thru (e) and thereafter emulsify a proper amount of warm component (a) therein using standard emulsifying procedures. The resulting emulsion has long term stability at the temperature commonly used during preparation, holding and pouring the emulsion. On cooling, the emulsion solidifies to a uniform, non-leaking antiperspirant stick with a dry feel.

The examples which follow illustrate the water-in-oil emulsion type compositions of the invention.

EXAMPLES 1 TO 8

Water-in-oil emulsion sticks were prepared by emulsifying a warm solution of 50 parts by weight of a 50% aqueous solution of aluminum chlorohydrate in warm solutiosn (50 parts by weight) of the ingredients described in the accompanying table. The resulting emulsions were then poured into molds and cooled.

A panel of 50 persons was used to evaluate the compositios 1 through 8 and a commercial antiperspirant stick product by a statistically designed experiment; see Federal Register, Dept. of Health, Education, and Welfare, *Antiperspirant Drug Products for Over-The-Counter Human Use*, Oct. 10, 1978. Data were obtained in a statistically designed experiment and rated against each other and the control using a scale of 1 to 10, the most efficacious product being assigned a rating of 10. Results are given in the accompanying table.

|  | EXAMPLES 1-8 | | | | | | | |
| --- | --- | --- | --- | --- | --- | --- | --- | --- |
|  | 1 | 2 | 3 | 4 | 5 | 6 | 7 | 8 |
| Aluminum chlorohydrate (50%) | 50.0 | 50.0 | 50.0 | 50.0 | 50.0 | 50.0 | 50.0 | 50.0 |
| Polyglyceryl-4-oleate | 2.0 | 2.0 | — | — | 2.0 | 2.0 | — | — |
| Polyglyceryl-4-isostearate | — | — | 2.0 | 2.0 | — | — | 2.0 | 2.0 |
| 2-Methyl-2,4-pentanediol | 2.0 | — | 2.0 | — | 2.0 | — | 2.0 | — |
| Stearic acid | — | — | — | — | 2.0 | 2.0 | 2.0 | 2.0 |
| Stearyl alcohol | 19.0 | 19.0 | 19.0 | 19.0 | 17.0 | 17.0 | 17.0 | 17.0 |
| Volatile silicone | 26.0 | 28.0 | 26.0 | 28.0 | 26.0 | 26.0 | 26.0 | 28.0 |
| Mineral oil | 1.0 | 1.0 | 1.0 | 1.0 | 1.0 | 1.0 | 1.0 | 1.0 |
| Antiperspirant efficacy rating | 1 | 5 | 8 | 6 | 6 | 3 | 10 | 5 |

Compositions (3) and (7), representing the present invention, are shown to be the most efficacious antiperspirant sticks. Increased efficacy due to 2-methyl-2,4-pentanediol is shown by compositions (7) compared to (8).

EXAMPLE 9

The procedure of Examples 1-8 was used to prepare a water-in-oil emulsion type antiperspirant stick having the following composition:

|  | Percent by Weight |
| --- | --- |
| Aluminum chlorohydrate (50%) | 45.0 |
| Volatile silicone | 26.1 |
| Stearyl alcohol | 17.0 |
| Polyglyceryl-4-isostearate | 2.2 |

-continued

| | Percent by Weight |
| --- | --- |
| Stearic acid (98+ %) | 2.0 |
| 2-Methyl-2,4-pentanediol | 2.0 |
| PPG-3-myristyl ether | 1.5 |
| Polyethylene 617A | 0.7 |
| Perfume | 0.5 |
| Water | 3.0 |
| | 100.0 |

What is claimed is:

1. An antiperspirant stick composition consisting essentially of:
   (a) 10 to 70 parts by weight of an aqueous solution of an astringent metal compound as a discontinuous phase dispersed in a solid matrix consisting essentially of
   (b) 0.1 to 35 parts by weight of a volatile cyclic dimethylsiloxane liquid,
   (c) 10 to 30 parts by weight of at least one solid alkanol containing at least 12 carbon atoms,
   (d) 1 to 5 parts by weight of a C4 to C8 alkanediol, and
   (e) 0.5 to 5 parts by weight of at least one C12 to C20 fatty acid ester of a polyglycerol, said ester having a resultant HLB value of 6 to 9; the total of (a) through (e) being 100 parts by weight.

2. An antiperspirant composition according to claim 1 or 2 wherein the component (d) is 2-methyl-2,4-pentanediol.

3. An antiperspirant composition according to claim 1 or 2 wherein component (e) is polyglyceryl-4-isostearate.

4. An antiperspirant composition according to claim 1, 2, or 3 wherein component (b) is a mixture of cyclic dimethylsiloxanes containing as a major proportion thereof decamethylcyclopentasiloxane.

5. An antiperspirant stick composition according to claim 1 including additional waxy materials.

6. An antiperspirant composition according to claim 4 which additionally comprises up to 5 parts by weight of an alkanoic acid containing at least 12 carbon atoms.

7. An antiperspirant composition, according to claim 1, wherein said metal compound is an aluminum, zirconium or zinc compound or a combination thereof.

* * * * *